United States Patent [19]
Cecchi

[11] Patent Number: 5,843,023
[45] Date of Patent: Dec. 1, 1998

[54] ASPIRATION NEEDLE WITH SIDE PORT

[76] Inventor: Michael Cecchi, 339 Barlett Dr., Madison, Conn. 06443

[21] Appl. No.: 539,231

[22] Filed: Oct. 4, 1995

[51] Int. Cl.$^6$ .................................................... A61M 5/00
[52] U.S. Cl. ............................................. 604/44; 604/272
[58] Field of Search .................................. 604/27, 35, 44, 604/158, 239, 272

[56] References Cited

U.S. PATENT DOCUMENTS

| | | | |
|---|---|---|---|
| 950,822 | 3/1910 | McElroy | 604/272 |
| 3,076,457 | 2/1963 | Copen | 604/272 |
| 4,016,879 | 4/1977 | Mellor | 604/27 |
| 4,098,275 | 7/1978 | Consalvo | 604/27 X |
| 4,299,217 | 11/1981 | Sagae et al. | 604/44 |
| 4,493,708 | 1/1985 | Sugisawa | 604/44 X |
| 4,531,935 | 7/1985 | Berryessa | 604/44 X |
| 5,160,319 | 11/1992 | Emery et al. | 604/27 |
| 5,203,769 | 4/1993 | Clement et al. | 604/35 X |

*Primary Examiner*—Sam Rimell
*Attorney, Agent, or Firm*—Wiggin & Dana

[57] ABSTRACT

A single-lumen oocyte collection device, having a cannula which extends axially outward from a proximal end of a hub. The cannula has a side port and an axial port, each linked to a resilient portion of tubing to allow selective occlusion of the lumen thereof. The side port, through the hub, has a fixed relation to a sharpened, bevelled tip of the cannula, allowing even rotation and accurate orientation of the beveled tip of the device to puncture a follicle on an ovary with minimal trauma prior to collecting an oocyte. An echogenic structure is formed at the tip of the cannula.

20 Claims, 4 Drawing Sheets

ASPIRATION NEEDLE WITH SIDE PORT

FIELD OF THE INVENTION

The present invention relates to devices for use in collecting an aspiration sample during a medical procedure, and more particularly to devices for collecting an oocyte from an ovary of a patient, for use in a surgically-assisted reproduction procedure, the device having a single-lumen needle and selectively occludable resilient tubing in line with both a main flow path and an auxiliary flow path.

BACKGROUND OF THE INVENTION

As known in U.S. Pat. No. 5,160,319, surgically-assisted reproduction techniques such as in vitro fertilization (IVF) and gamete intrafallopian transfer (GIFT) have become widely accepted clinical methods for the treatment of infertility.

IVF involves the fertilization of a female oocyte or egg in vitro (outside of the womb). With GIFT, fertilization occurs in vivo (within the womb). Various procedures are employed, in which oocytes are retrieved from ovarian follicles (sac-like structures on the ovaries that contain the oocytes) by either a laparoscopic or transvaginal procedure using an aspiration needle. In general, these methods are performed under ultrasonic guidance with a transvaginal probe. During an oocyte retrieval procedure, a relatively long aspiration needle is either vaginally or abdominally inserted into a patient so that the distal end of the needle is in contact with a patient's ovary. The objective is to puncture an individual follicle on the ovary and withdraw the contents of a follicle, including a single or many oocytes, up through the needle. Generally, the proximal end of the needle is connected to flexible tubing which is, in turn, connected through a test tube to a vacuum source. The vacuum source provides suction through both the tubing and the needle to allow aspiration of the oocyte from the follicle, into the test tube, where the oocyte is collected. The test tube configuration acts as a trap to prevent loss of the oocyte into the vacuum system.

As follicular fluid is aspirated, it travels through the needle and tubing into the test tube. The contents of the test tube are periodically examined microscopically to determine whether an oocyte is present. In some instances, the oocyte may become lodged in the needle or in the follicle and is not easily aspirated. In such instances, it may be necessary to irrigate the follicle and needle to dislodge the oocyte and allow aspiration of the oocyte into the test tube.

Two different needle styles are currently used for oocyte retrievals. One needle style is a single-lumen device. This style requires that any irrigation that is performed be conducted through the same fluid path (or lumen) of the cannula that is used for aspiration. In such instances, if an oocyte is lodged in the fluid path, the oocyte may be actually flushed back into the follicle during the irrigation procedure. Known single lumen systems have a complex valving configuration to control flow. Therefore, the use of known configuration single-lumen devices may create the potential of losing the oocyte during the irrigation procedure. In practice, transparent tubing improves the visual feedback of the status of the procedure. Single lumen systems allow the use of an overall smaller cannula, less costly construction and a very sharp beveled tip.

Some physicians prefer the use of a dual-lumen device for oocyte collection procedures. A dual-lumen device has a first fluid path, or lumen, for aspiration and a second fluid path for irrigation. The use of separate paths creates a complex structure with two unidirectional flow paths, reducing the possibility of flushing an oocyte out of the aspiration path during an irrigation procedure. Dual lumen systems are larger, for example 16 Ga. minimum, more complex and therefore costly, and more difficult to apply to small biological structures. See, U.S. Pat. Nos. 4,270,535; 4,203,436; 4,134,402; 4,098,275; 4,073,297; and 4,016,879 for various dual lumen catheter systems.

As discussed above, each oocyte is located in a fluid-filled sac or follicle. Before an oocyte can be retrieved, a physician needs to be able to accurately locate and puncture each sac prior to retrieval without damaging or losing the oocyte. In order to cleanly puncture the sac, oocyte collection devices generally include a cannula having a sharpened beveled tip. Ideally, the tip is gently inserted into the follicle to puncture the sac and release the oocyte.

In order to visualize the sharpened tip of the cannula simultaneously with the follicle, it is known to provide an echogenic structure near the tip of the cannula.

It is very important that as the device is manually rotated the physician knows the orientation of the beveled tip. Therefore, known systems include an asymmetric handle for easily determining the orientation of the beveled tip and to provide a means for allowing a physician to evenly rotate the tip.

Known oocyte collection devices may include a cannula which extends radially outwardly, i.e., a side port. Generally, radially extending cannula ports with stiff traditional tubing connection may make it difficult for a physician to evenly rotate the device without traumatizing the patient's ovary. If a patient's ovary is traumatized, it may further complicate the patient's ability to conceive. Thus, it is critical to evenly rotate an oocyte collection device and, thus, be able to retrieve an oocyte without traumatizing a patient's ovary.

SUMMARY OF THE INVENTION

The present invention provides a single lumen aspiration needle having a structure to allow well-controlled rotation by a surgeon, with simplified control over fluid flows. A thin cannula having a sharp beveled tip is provided. An echogenic structure, e.g., a series of closely spaced ridges, are formed near the tip to disperse ultrasonic waves for localization under ultrasonic guidance. Because the cannula has a single lumen for a given cannula diameter the cross section of the lumen will be greater than for a multiple lumen device. The interior of the cannula is smooth, thereby minimizing the probability that an oocyte will become lodged in the tube.

Both axially and radially extending ports are provided opposite the beveled tip of the cannula. The radial port is provided as a concentric structure around the cannula, a distance away from the terminus. The wall of the cannula is cut with a rectangular groove, directed at an approximately 45°–60° angle away from the beveled tip, approximately half the diameter of the cannula. The bevel of the tip is formed at approximately 20° angle from the opposite side.

The radially extending port and the axially extending port are preferably both provided in a single rigid "T" connector, which is further linked with a length of resilient tubing. Thus tubing is, for example, a medical grade silicone rubber tube. The resilient tubing, in turn, is connected to a length of fine bore Teflon tubing. The axially extending port tubing is connected to a dual hole stopper for a test tube trap, which in turn, is connected to a vacuum source. The radially extending port tubing terminates in a Luer lock hub.

In the preferred embodiment, the cannula is formed of 304 grade stainless steel. In the preferred embodiment, the tube connecting the resilient conduit to the Luer lock connector is Teflon. Alternatively, other polymeric tubing which is sterilizable by gamma irradiation may be used.

In use, the resilient tubing sections allow fine modulation of the flows by the surgeon. A simple kink in the tubing will restrict all flow, so it is preferred that the resilient tubing sections be relatively short. By slowly unkinking or releasing external pressure on the tubing, the flow may be finely modulated. In order to draw aspirate through the cannula lumen, the side port path is occluded, and the vacuum is applied to the cannula tip. In order to flush the cannula lumen, the axially extending port path is occluded, and fluid flushed from the side port retrograde down the lumen, to instill media into the follicle or cyst.

By providing direct control over flows through the hand of the surgeon, the "feel" and responsiveness of the device is improved over mechanically valved systems. Of course, an external mechanical force may be applied to the resilient tubing in order to control the flows, such as a tube clamp, should the surgeon so desire. This may be appropriate during extended pauses, or where tube flushing is desired.

The angle of the radially extending port aperture assists in preventing sticking of the oocyte or debris, ensuring smooth flow or material through to the test tube trap.

It is therefore an object of the present invention to provide a medical aspiration device, comprising a cannula having a distal sharpened beveled tip and a proximal portion; an indicator at the proximal portion corresponding to an orientation of the sharpened beveled tip; a multi-port connector at the proximal portion, allowing flow from the proximal portion through each of a plurality of ports; and a resilient conduit, having a flow path in communication with one of the ports, selectively occluded by an externally applied force.

It is also an object according to the present invention to provide the aspiration device further comprising, at each of the plurality of ports, a resilient conduit, having a flow path selectively occluded by an externally applied force.

According to the present invention, the multi-port connector preferably comprises a "T" connector having an axial port and a radial port. Further, the proximal portion of the cannula may comprise an axial end aperture and a radial wall aperture formed a small distance from the proximal portion.

It is another object of the present invention to provide an aspiration device having a resilient conduit formed of a silicone tube, which has a lumen cross section which is responsive to an external applied force.

It is a still further object according to the present invention to provide an aspiration device wherein the distal sharpened beveled tip comprises an echogenic structure.

It is a still further object of the present invention to provide a medical aspiration device, comprising a cannula having a distal sharpened beveled tip and a proximal portion; an indicator at the proximal portion corresponding to an orientation of the sharpened beveled tip; a multi-port connector at the proximal portion, allowing flow from the proximal portion through each of a plurality of ports; and a resilient conduit, having a flow path in communication with one of the ports, selectively occluded by an externally applied pressure, the multi-port connector comprising a "T" connector having an axial port and a radial port, wherein the proximal portion of the cannula comprises an axial end aperture and a radial wall aperture, distal from the proximal portion, further comprising, in communication with each of the axial end aperture and the radial wall aperture, a resilient conduit having a flow path selectively occluded by an externally applied pressure.

The aspiration device may also comprise a member having multiple flat outer surfaces which form a polygon, in which one flat surface or vertex corresponds to the sharpened beveled tip. The cannula is preferably formed of stainless steel. The resilient conduit is preferably substantially transparent, for visual feedback of the operation of the device.

In order to localize the external pressure sensitivity, the resilient conduit may be formed in series with a flexible collapse resistant conduit.

For a full understanding of the present invention, reference should now be made to the following detailed description of the preferred embodiments of the invention as illustrated in the accompanying drawings.

BRIEF DESCRIPTION OF THE DRAWINGS

The preferred embodiments of the invention will be shown by way of drawings of the Figures, in which.

DESCRIPTION OF THE PREFERRED EMBODIMENTS

Figure 1:
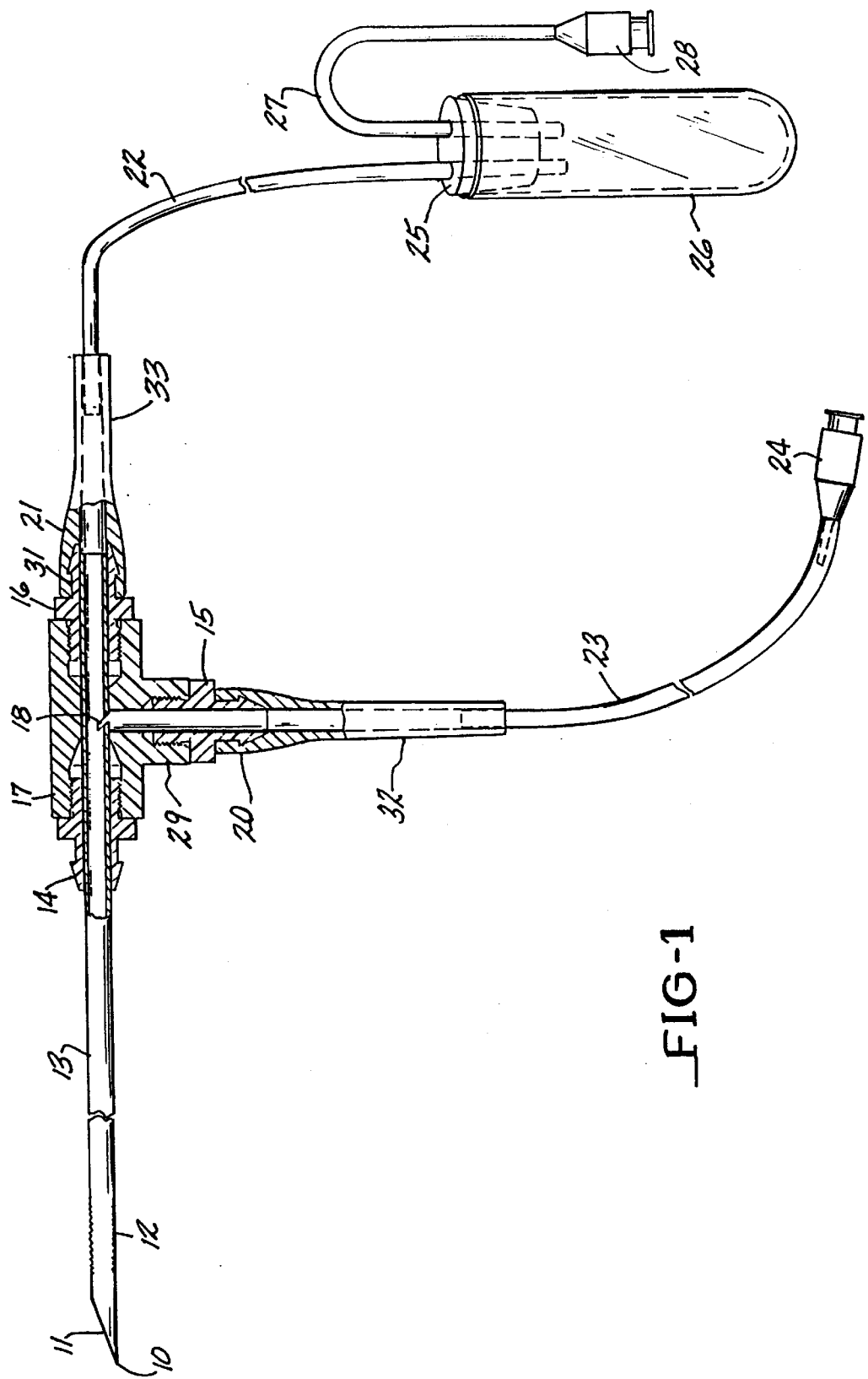
FIG. 1 is a perspective view of a preferred embodiment of the invention.

The preferred embodiments of the present invention will now be described with reference to the Figures. Identical elements in the various figures of the present invention are designated with the same reference numerals.

Figure 2:
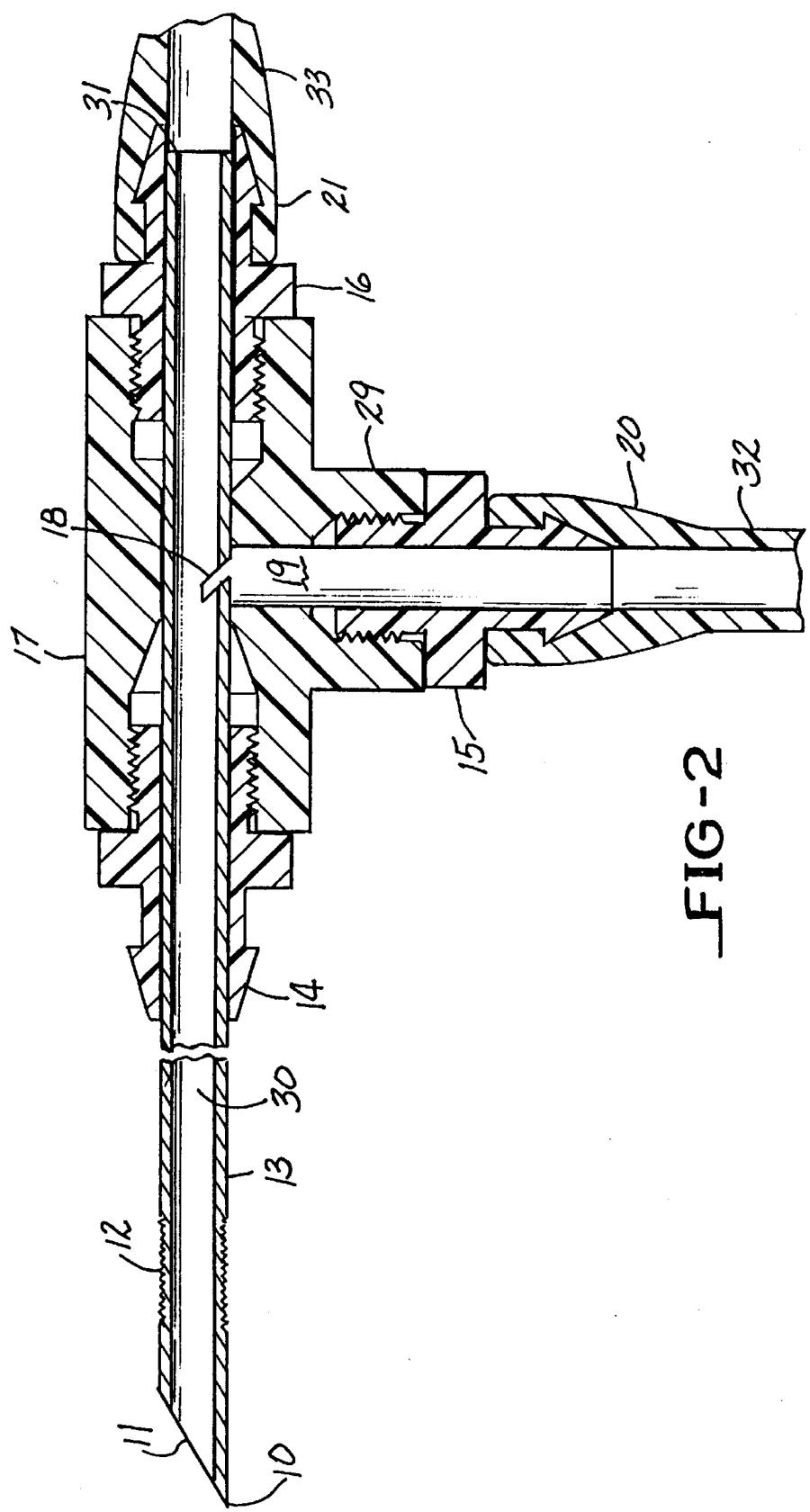
FIG. 2 is a cross-sectional view of embodiment of FIG. 1 illustrating the fluid aspiration channel at the "T" junction.

As shown in FIGS. 1 and 2, a single lumen 17 Ga. cannula 13, having a sharp beveled tip 10, with echogenic members 12, is provided. The proximal portion of the cannula 13 is provided with a cut groove 18, aligned with a radial port 29 of a T-connector 17. The radial port 29 is connected to a Teflon tube 23 through a resilient conduit 20 formed of silicone rubber. The Teflon tube 23 is terminated with a Luer lock connector 24.

The axial port 16 of the T-connector 17 is also connected to a Teflon tube 22 through a resilient conduit 21 formed of a silicone rubber segment. The Teflon tube 22 is inserted through a dual aperture silicone rubber stopper 25 for a test tube 26. The other aperture of the stopper 25 has a Teflon tube 27 inserted, which terminates in a Luer lock connector 28. The single lumen cannula 13 extends between about 23–36 cm. The echogenicity of the sharpened beveled tip 10 is increased by an echogenic portion 12 having spiral or parallel circumferential "V"-shaped grooves approximately 0.75 mm apart near the sharpened beveled tip 10.

Approximately 1.5 cm from the proximal portion 31 of the single lumen cannula 13, a cut groove 18 is formed in one side of the cannula 13 tubing, approximately 0.5 mm wide by 0.5 mm deep, formed at a 45°–60° angle to the cannula 13, toward the sharpened beveled tip 10.

The "T"-shaped connector 17 is preferably a polycarbonate plastic, with threaded tube connectors 14, 15, 16 holding the resilient conduit 20, 21 silicone tubing and single lumen cannula 13.

The resilient conduit 20, 21 silicone tubing allows external compression or flexing at a respective position 32, 33 to cut off flow and selectively provide flow from the axial and/or perpendicular ports. The resilient conduit 20, 21 silicone rubber tubing has sufficient body to prevent collapse under the aspiration vacuum. For example, approximately 1 mm OD, 3 mm ID, 60 mm long tubing may be used. The Teflon tubing 22, 23 has approximately 1 mm ID and 1.5 mm OD, thereby providing a force fit in the resilient conduit 20, 21 silicone tubing.

Figure 3:
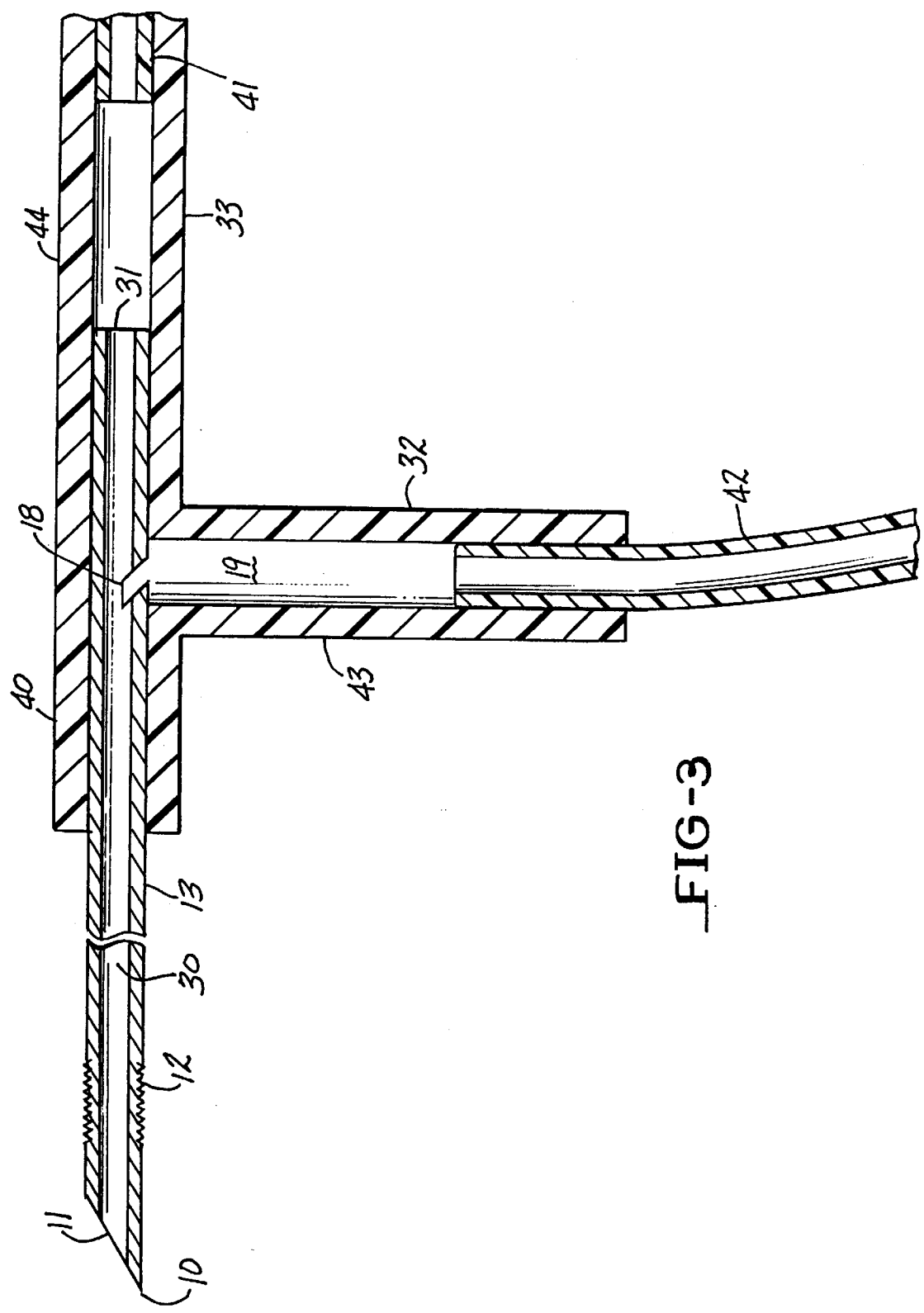
FIG. 3 is a cross section of a first alternative embodiment of the invention.

In a first alternative embodiment, shown in FIG. 3, the "T"-shaped connector 40 and resilient conduit 43, 44 are integral, with lengths of thin stiff tubing 41, 42 inserted within the lumen of the resilient conduit 43, 44. The steel cannula 13 is inserted into the "T"-shaped connector 40, with the bevel 11 aligned in fixed relation to the radial port 19.

Figure 4:
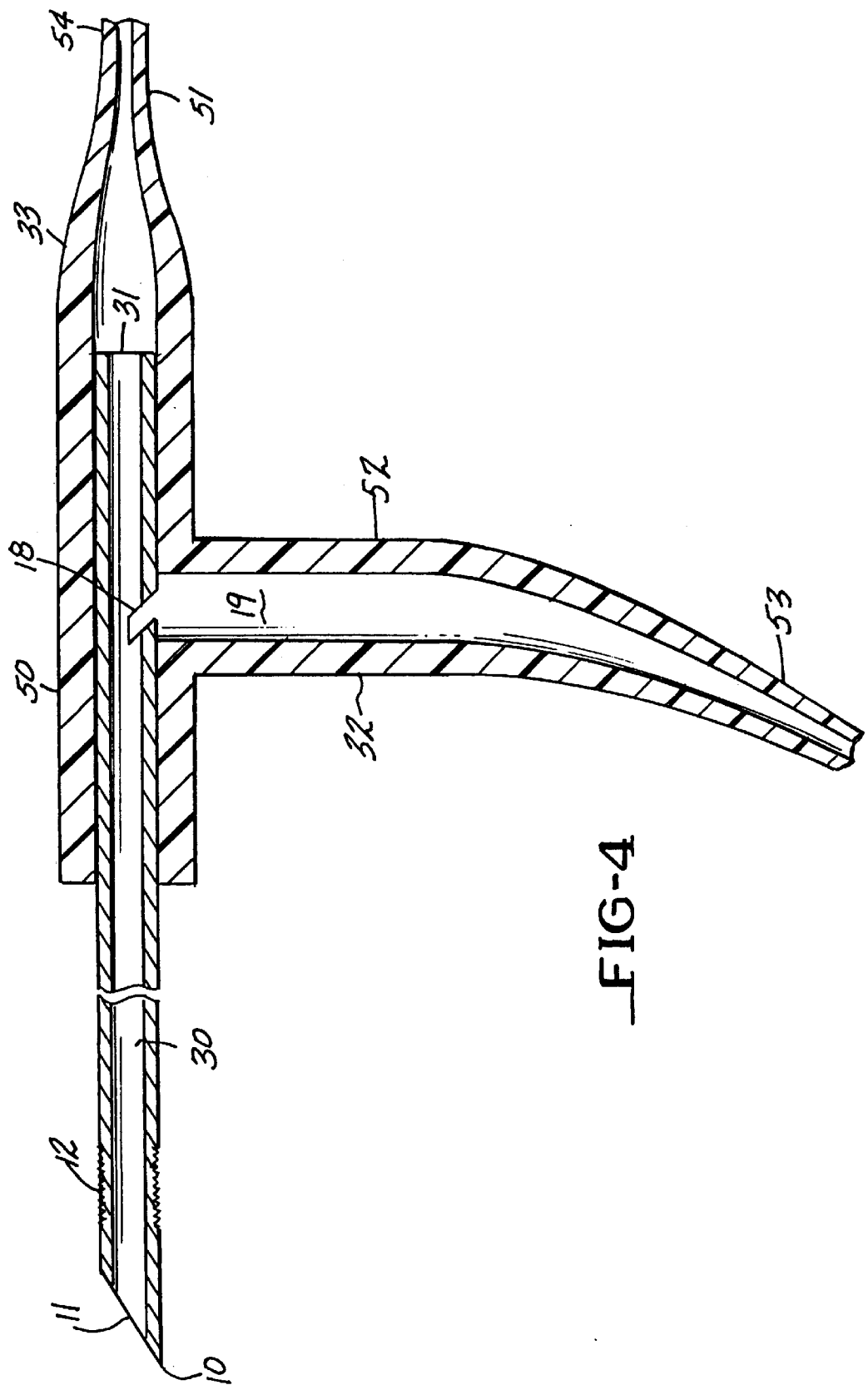
FIG. 4 is a cross section of a second alternative embodiment of the invention.

In a second alternative embodiment, shown in FIG. 4, the "T"-shaped connector 50, resilient conduit 51, 52 and extension tubing 53, 54 are integral. As with the first alternate embodiment, the steel cannula 13 is inserted into the "T"-shaped connector 50, with the bevel 11 aligned in fixed relation to the radial port 19.

In use, the single lumen cannula 13 is provided as an aspiration biopsy needle. The radial port 19, however, may be used to inject saline or other media into the biopsy area in order to free oocytes in a follicle or debris in a cyst. During fluid infusion, the axial port resilient conduit 21 is occluded at the clamping portion 33, shunting the infused fluid through the cannula 13 into the patient. During normal use, the radial port resilient conduit 20 is occluded at the clamping portion 32 by an external pressure or flex to prevent draw of media into the cut groove 18 and leakage of the aspiration vacuum.

During on oocyte retrieval procedure, the sharpened beveled tip 10 of the cannula 13 is inserted into the patient's pelvic cavity and directed to the ovarian follicle using either laparoscopic or ultrasound guidance. The cannula 13 can be inserted transabdominally using a laparoscope for visualization or transvaginally under ultrasound guidance. A cannula guide may be provided on a transvaginal probe to facilitate use. Once it has been determined that the distal end of the cannula 13 is located in the area of a follicle, the sharpened beveled tip 10 of the device is gently inserted into the follicle. Immediately after the distal end of the cannula enters the follicle, a vacuum is applied to the aspiration channel of the axial port 31 to aspirate the oocyte and any follicular fluid. This vacuum may be supplied by activating a vacuum pump or withdrawing the plunger of a syringe. During the aspiration procedure, the device may be gently rotated so that the beveled sharpened tip 10 gently scrapes the internal follicle wall to dislodge the oocyte. This rotation is called intrafollicular curettage. Since it is important not to damage any adjacent follicles which may contain other oocytes and not to traumatize the patient's ovary, it is critical that this rotation procedure be finely controlled and performed very evenly. Therefore, it is highly advantageous to provide a device in which the location of the beveled point can be accurately determined.

The device preferably provides a "T"-shaped connector 17 having a polygonal cross section and a fixed relation between the radial port 19 and the bevel 11. The orientation of the sharpened beveled tip 10 corresponding to the radial port 19 allows the physician to accurately determine the actual location and orientation of the point and estimate the depth of needle penetration.

There has thus been shown and described novel aspects of surgical aspiration needles, which fulfill the objects and advantages sought therefor. Many changes, modifications, variations, combinations, subcombinations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the appended claims.

What is claimed is:

1. A medical aspiration device, comprising:
   (a) a single lumen cannula having a hollow space, a distal sharpened beveled tip and a proximal portion;
   (b) an indicia at said proximal portion corresponding to an orientation of said sharpened beveled tip;
   (c) a connector at said proximal portion having a pair of ports, providing a flow path through said hollow space of said single lumen cannula, from said distal sharpened beveled tip, through said proximal portion and through each of said pair of ports; and
   (d) a resilient conduit, having a flow path in communication with one of said pair of ports, having a first portion defined by a first wall, said first portion being selectively occludable to restrict a flow therethrough by application of an externally applied force to said first wall, and a second portion defined by a second wall, said second portion resisting occlusion by an externally applied force to said second wall, said second portion of said resilient conduit maintaining patency when subject to a force which occludes said first portion.

2. The aspiration device according to claim 1 wherein a resilient conduit is provided at each of said pair of ports.

3. The aspiration device according to claim 1, wherein said multi-port connector comprises a "T" connector having an axial port and a radial port.

4. The aspiration device according to claim 3, wherein said proximal portion of said cannula comprises an axial end aperture and a radial wall aperture, spaced from said axial end aperture, further comprising, in communication with each of said axial end aperture and said radial wall aperture, a resilient conduit.

5. The aspiration device according to claim 4, wherein said resilient conduit in communication with said axial end aperture is substantially transparent.

6. The aspiration device according to claim 5, further comprising a flexible collapse resistant conduit in communication with each of said resilient conduits.

7. The aspiration device according to claim 1, wherein said proximal portion of said cannula comprises an axial end aperture and a radial wall aperture, spaced from said axial end aperture.

8. The aspiration device according to claim 1, wherein said resilient conduit comprises a silicone tube.

9. The aspiration device according to claim 1, wherein said resilient conduit is substantially transparent.

10. The aspiration device according to claim 1, wherein said distal sharpened beveled tip comprises an echogenic structure.

11. The aspiration device according to claim 1, wherein said cannula is formed of stainless steel.

12. The aspiration device according to claim 1, wherein said indicator comprises a member having multiple flat outer surfaces which form a polygon in which one flat surface or vertex corresponds to said sharpened beveled tip.

13. A method for aspirating a biological sample comprising the steps of:
   (a) providing a single lumen cannula having a hollow space, a distal sharpened beveled tip and a proximal portion; an indicia at the proximal portion corresponding to an orientation of the sharpened beveled tip; a connector at the proximal portion having a pair of ports, providing a flow path through the hollow space of the single lumen cannula, from the distal sharpened beveled tip, through the proximal portion and through each of the pair of ports; and a resilient conduit, having a flow path in communication with one of the pair of ports, having a first portion defined by a first wall, the first portion being selectively occludable to restrict a flow there through by application of an externally applied force to the first wall, and a second portion defined by a second wall, the second portion resisting occlusion by an externally allied force to the second wall, the second portion of the resilient conduit maintaining patency when subject to a force which occludes the first portion;

(b) placing the sharpened beveled tip proximate to a location of the biological sample and inserting the sharpened beveled tip in the biological sample;

(c) drawing a vacuum at one of the ports;

(d) applying a force to the first wall of the resilient conduit sufficient to restrict a flow through the resilient conduit; and (e) injecting media through the other of the ports into the hollow space of the single lumen cannula.

14. A medical aspiration device, comprising:

(a) a cannula having a wall, a hollow space, a distal sharpened beveled tip, a proximal portion having an axial aperture and a lateral aperture;

(b) an axial port, in fluid communication with said hollow space through said axial aperture;

(c) a lateral port, in fluid communication with said hollow space, in fluid communication with said hollow space through said lateral aperture, sad lateral aperture being formed as a groove in said wall of said cannula inclined with respect to said distal sharpened beveled tip;

(d) an axial conduit, having a flow path in communication with said axial port, having a wall; and (e) a lateral conduit, having a flow path in communication with said lateral port, having a wall, said axial conduit and lateral conduit each being selectively occludable by an externally applied force.

15. The aspiration device according to claim 14, wherein said groove is inclined inward toward said distal tip at an angle of between 45°–60° to a central axis of said cannula.

16. The aspiration device according to claim 14, wherein at least one of said conduits comprises silicone rubber tubing.

17. The aspiration device according to claim 14, wherein said axial conduit, lateral conduit and cannula converge at a "T" connector, said lateral conduit emerging at right angles to said axial conduit and said cannula.

18. The aspiration device according to claim 14, further comprising an elongated conduit, joining one of said conduits and being in fluid communication therewith, said elongated conduit maintaining patency when subject to said force which occludes one of said conduits.

19. The aspiration device according to claim 14, wherein said grooved wall cannula provides an unobstructed path for an oocyte from said distal tip through said axial port.

20. The aspiration device according to claim 7, said radial wall aperture being formed as a groove in said cannula included inward toward said sharpened beveled tip at an angle of between 45°–60° to said cannula.

* * * * *